(12) United States Patent
Irie et al.

(10) Patent No.: US 7,161,151 B2
(45) Date of Patent: Jan. 9, 2007

(54) PLASTIC IDENTIFYING METHOD

(75) Inventors: Shouichi Irie, Toyonaka (JP); Teruo Gotou, Takatsuki (JP); Takao Hisazumi, Ibaraki (JP); Hiroshi Iwamoto, Toyonaka (JP); Hiroyuki Tokumasu, Hirakata (JP); Toshio Shimamura, Ibaraki (JP)

(73) Assignee: Matsushita Eco Technology Center Co., Ltd., Hyogo (JP)

( * ) Notice: Subject to any disclaimer, the term of this patent is extended or adjusted under 35 U.S.C. 154(b) by 50 days.

(21) Appl. No.: 10/476,637

(22) PCT Filed: Nov. 25, 2002

(86) PCT No.: PCT/JP02/12290

§ 371 (c)(1),
(2), (4) Date: Oct. 28, 2003

(87) PCT Pub. No.: WO03/046523

PCT Pub. Date: Jun. 5, 2003

(65) Prior Publication Data

US 2004/0149911 A1 Aug. 5, 2004

(30) Foreign Application Priority Data

Nov. 28, 2001 (JP) ............................. 2001-362213

(51) Int. Cl.
*G01J 5/02* (2006.01)

(52) U.S. Cl. .............................................. 250/339.12
(58) Field of Classification Search ............ 250/339.12
See application file for complete search history.

(56) References Cited

U.S. PATENT DOCUMENTS 3,855,277 A * 12/1974 Fox ............................ 524/409

(Continued)

FOREIGN PATENT DOCUMENTS

DE 195 02 134 8/1996

(Continued)

*Primary Examiner*—Otilia Gabor
*Assistant Examiner*—Christine Sung
(74) *Attorney, Agent, or Firm*—Hamre, Schumann, Mueller & Larson, P.C.

(57) ABSTRACT

A plastic identifying method of the present invention is provided with a step (i) of obtaining a first infrared absorption spectrum by irradiating infrared light of a predetermined wave number onto an item to be identified that contains plastic and measuring the intensity of the infrared light that is totally reflected by this item, and a step (ii) of identifying the plastic contained in the item to be identified by matching the first infrared absorption spectrum with a group of infrared absorption spectra that have been measured for predetermined materials, wherein the predetermined materials are a group of materials containing plastics, and each infrared absorption spectrum in this group of infrared absorption spectra is obtained by irradiating infrared light of a predetermined wave number onto a predetermined material, and measuring the intensity of the infrared light that is totally reflected by that material, and matching is carried out by comparing peaks in the first infrared absorption spectrum with peaks in each infrared absorption spectrum in the group of infrared absorption spectra. With this plastic identifying method, items that contain plastic can be identified accurately, even in such cases as when the items have been colored or contain additives or the like.

23 Claims, 4 Drawing Sheets

U.S. PATENT DOCUMENTS

| | | | |
|---|---|---|---|
| 4,636,435 A | * | 1/1987 | Yanagihara et al. ........ 428/336 |
| 4,890,577 A | | 1/1990 | Maibach |
| 4,980,454 A | * | 12/1990 | Tamai et al. ................. 528/362 |
| 5,091,647 A | | 2/1992 | Carduner et al. |
| 5,216,244 A | | 6/1993 | Esaki et al. |
| 5,510,619 A | | 4/1996 | Zachmann et al. |
| 5,512,752 A | * | 4/1996 | Aikawa et al. ........ 250/339.12 |
| 5,777,330 A | | 7/1998 | Murase et al. |
| 5,965,889 A | | 10/1999 | Brierley |
| 6,108,077 A | | 8/2000 | Heaton et al. |
| 6,335,376 B1 | | 1/2002 | Allen et al. |
| 6,518,572 B1 | | 2/2003 | Kishii et al. |
| 6,563,119 B1 | * | 5/2003 | Zoidis ................... 250/339.07 |
| 6,610,981 B1 | | 8/2003 | Sommer, Jr. |
| 6,845,869 B1 | | 1/2005 | Graf von Deym et al. |
| 6,852,977 B1 | | 2/2005 | Hisazumi et al. |

FOREIGN PATENT DOCUMENTS

| | | |
|---|---|---|
| EP | 1 286 153 | 2/2003 |
| JP | 64-6761 | 1/1989 |
| JP | 5-273122 | 10/1993 |
| JP | 7-239297 | 9/1995 |
| JP | 8-136449 | 5/1996 |
| JP | 10-154734 | 6/1998 |
| JP | 11-211634 | 8/1999 |
| JP | 2000-186987 | 7/2000 |
| JP | 2000-199734 | 7/2000 |
| JP | 2000-214084 | 8/2000 |
| JP | 2001-122978 | 5/2001 |
| JP | 2001-194297 | 7/2001 |
| JP | 2002-286637 | 10/2002 |

* cited by examiner

PLASTIC IDENTIFYING METHOD

TECHNICAL FIELD

The present invention relates to plastic identifying methods.

BACKGROUND ART

Plastics have many strong points, such as being lightweight and strong, capable of transparency and non-permeability to water or gases, easily colored and shaped, and due to their high usability, their production volumes and usage volumes are also increasing. However, accompanying this, the volumes of discarded plastics have been increasing, and the increased burden on the environment has become a social problem. To solve these problems and also to use limited resources more effectively, there has been intensive research in recent years on methods of recycling plastics.

Methods of recycling plastics include, for example: material recycling, in which plastics are repelleted and used as raw material for new molded products; thermal recycling, in which plastics are combusted and the thermal energy recovered; and chemical recycling, in which plastics are thermally decomposed for use as reduction agents for blast furnaces, or decomposed down to fats/oils or monomers and reused as raw materials for plastics.

Among these, material recycling can be said to be the most desirable method, as it requires only a small amount of energy for recycling. However, in order to prevent the recycled plastics from having reduced physical properties, it is necessary to prevent the mixture of different plastic types when the plastics are repelleted. Therefore, there is a need for a highly accurate method of identifying plastics.

Conventionally, the main methods used for identifying plastic types are spectroscopic methods such as infrared spectroscopy using near infrared light. However, with these spectroscopic methods, identification is difficult when the plastics to be identified are dark-coloured plastics (for example, the plastics used for such items as the chassis of television receivers and many other household electrical appliances are colored black), because of reasons such as the applied near infrared light being absorbed, and it is therefore difficult to obtain infrared absorption spectra.

Furthermore, when identifying plastic types using obtained infrared absorption spectra, it is usual to compare and match the obtained infrared absorption spectra with a group of infrared absorption spectra of various standard plastics. The process of comparing and matching involves searching for the infrared absorption spectrum of a standard plastic that is the best fit with the obtained infrared absorption spectrum, and thereby identifying the type of plastic.

Very often plastics that are to be recycled contain flame retardants and other additives. However, the standard plastics that have been compared and matched are basically "pure" polymers, and plastics that contain additives have not been included as objects of comparison and matching. Furthermore, the data for the infrared absorption spectra of standard plastics usually have been data obtained by penetrating infrared light through the items to be identified (penetration method).

DISCLOSURE OF INVENTION

In view of these circumstances, it is an object of the present invention to provide a plastic identifying method that enables plastics to be identified accurately, even in such cases as when the items to be identified have been colored or contain additives or the like.

To achieve this object, the plastic identifying method of the present invention includes:

(i) a step of obtaining a first infrared absorption spectrum by irradiating infrared light of a predetermined wave number onto an item to be identified that contains plastic and measuring the intensity of the infrared light that is totally reflected by this item, and;

(ii) a step of identifying the plastic contained in the item to be identified by matching the first infrared absorption spectrum with a group of infrared absorption spectra that have been measured for a group of predetermined materials, wherein the group of predetermined materials is a group of materials containing plastics, and each infrared absorption spectrum in the group of infrared absorption spectra is obtained by irradiating infrared light of a predetermined wave number onto each material included in the group of predetermined materials, and measuring the intensity of the infrared light that is totally reflected by that material, and matching is carried out by comparing peaks in the first infrared absorption spectrum with peaks in each infrared absorption spectrum in the group of infrared absorption spectra.

The step (i) of the plastic identifying method also may include:

(i-a) a step of sampling a test piece from the item to be identified; and (i-b) a step of obtaining the first infrared absorption spectrum by irradiating infrared light of a predetermined wave number onto the test piece, and measuring the intensity of the infrared light that is totally reflected by the test piece.

The step (i) of the plastic identifying method also may include:

(i-A) a step of sampling a test piece from the item to be identified;

(i-B) a step of obtaining a second infrared absorption spectrum by irradiating infrared light of a predetermined wave number onto a first face of the test piece that corresponds to a surface of the item to be identified, and measuring the intensity of the infrared light that is totally reflected by the first face, and (i-C) a step of obtaining the first infrared absorption spectrum by irradiating infrared light of a predetermined wave number onto a second face of the test piece that was first exposed when the test piece was sampled, and measuring the intensity of the infrared light that is totally reflected by the second face.

The predetermined group of materials in the plastic identifying method may be a group of materials that contains at least one material selected from the group consisting of acrylonitrile-butadiene-styrene copolymers, polypropylenes, and polystyrenes.

The predetermined group of materials in the plastic identifying method may be a group of materials containing plastics that contain flame retardants.

The plastics that contain flame retardants in the plastic identifying method may be acrylonitrile-butadiene-styrene copolymers that contain tetrabromobisphenol A (TBA) series flame retardants.

The plastics that contain flame retardants in the plastic identifying method may be polystyrenes that contain at least one of the flame retardants selected from the group consisting of decabrominated flame retardants, TBA series flame retardants, triazine series flame retardants, and ethylenebis series flame retardants.

In the step (ii) of the plastic identifying method, when the first infrared absorption spectrum has a peak in the wave number range of 906 $cm^{-1}$ to 914 $cm^{-1}$, the wave number range of 1,023 $cm^{-1}$ to 1,031 $cm^{-1}$, and the wave number range of 2,234 $cm^{-1}$ to 2,242 $cm^{-1}$, and the value obtained by dividing the highest peak intensity in the wave number range of 1,000 $cm^{-1}$ to 1,008 $cm^{-1}$ by the highest peak intensity in the wave number range of 1023 $cm^{-1}$ to 1,031 $cm^{-1}$ is not greater than 0.5, then the item to be identified may be identified as an acrylonitrile-butadiene-styrene copolymer.

In the step (ii) of the plastic identifying method, when the first infrared absorption spectrum has a peak in the wave number range of 1,373 $cm^{-1}$ to 1,381 $cm^{-1}$, the wave number range of 2,913 $cm^{-1}$ to 2,921 $cm^{-1}$, and the wave number range of 2,946 $cm^{-1}$ to 2,954 $cm^{-1}$, then the item to be identified can be identified as a polypropylene.

In the step (ii) of the plastic identifying method, when the first spectrum has a peak in the wave number range of 1,368 $cm^{-1}$ to 1,376 $cm^{-1}$ and the wave number range of 1,023 $cm^{-1}$ to 1,031 $cm^{-1}$, and the value obtained by dividing the intensity of the highest peak in the wave number range of 1,000 $cm^{-1}$ to 1,008 $cm^{-1}$ by the intensity of the highest peak in the wave number range of 1,023 $cm^{-1}$ to 1,031 $cm^{-1}$ is not greater than 0.5, then the item to be identified can be identified as a polystyrene that does not contain a TBA series flame retardant.

In the step (ii) of the plastic identifying method, when the first spectrum has a peak in the wave number range of 1,368 $cm^{-1}$ to 1,376 $cm^{-1}$ and the wave number range of 1,023 $cm^{-1}$ to 1,031 $cm^{-1}$, and does not have a peak in the wave number range of 1,348 $cm^{-1}$ to 1,356 $cm^{-1}$, and the value obtained by dividing the intensity of the highest peak in the wave number range of 1,000 $cm^{-1}$ to 1,008 $cm^{-1}$ by the intensity of the highest peak in the wave number range of 1,023 $cm^{-1}$ to 1,031 $cm^{-1}$ is not greater than 0.5, then the item to be identified can be identified as a polystyrene that does not contain a flame retardant.

In the step (ii) of the plastic identifying method, when the first spectrum has a peak in the wave number range of 1,349 $cm^{-1}$ to 1,357 $cm^{-1}$ and the wave number range of 1,023 $cm^{-1}$ to 1,031 $cm^{-1}$, and does not have a peak in the wave number range of 907 $cm^{-1}$ to 915 $cm^{-1}$, and the value obtained by dividing the intensity of the highest peak in the wave number range of 1,000 $cm^{-1}$ to 1,008 $cm^{-1}$ by the intensity of the highest peak in the wave number range of 1,023 $cm^{-1}$ to 1,031 $cm^{-1}$ is not greater than 0.5, then the item to be identified can be identified as a polystyrene that contains decabrominated flame retardant.

In the step (ii) of the plastic identifying method, when the first spectrum has a peak in the wave number range of 1,000 $cm^{-1}$ to 1,008 $cm^{-1}$ and the wave number range of 1,023 $cm^{-1}$ to 1,031 $cm^{-1}$, and the value obtained by dividing the intensity of the highest peak in the wave number range of 1,000 $cm^{-1}$ to 1,008 $cm^{-1}$ by the intensity of the highest peak in the wave number range of 1,023 $cm^{-1}$ to 1,031 $cm^{-1}$ is at least 0.5, then the item to be identified can be identified as a polystyrene that contains a TBA series flame retardant.

In the step (ii) of the plastic identifying method, when the first spectrum has a peak in the wave number range of 1,356 $cm^{-1}$ to 1,364 $cm^{-1}$, the wave number range of 1,227 $cm^{-1}$ to 1,235 $cm^{-1}$, the wave number range of 1,085 $cm^{-1}$ to 1,093 $cm^{-1}$ and the wave number range of 1,023 $cm^{-1}$ to 1,031 $cm^{-1}$, and the value obtained by dividing the intensity of the highest peak in the wave number range of 1,000 $cm^{-1}$ to 1,008 $cm^{-1}$ by the intensity of the highest peak in the wave number range of 1,023 $cm^{-1}$ to 1,031 $cm^{-1}$ is not greater than 0.5, then the item to be identified can be identified as a polystyrene that contains a triazine series flame retardant.

In the step (ii) of the plastic identifying method, when the first spectrum has a peak in the wave number range of 1,369 $cm^{-1}$ to 1,377 $cm^{-1}$, the wave number range of 1,137 $cm^{-1}$ to 1,145 $cm^{-1}$, the wave number range of 742 $cm^{-1}$ to 750 $cm^{-1}$, and the wave number range of 1,023 $cm^{-1}$ to 1,031 $cm^{-1}$, and the value obtained by dividing the intensity of the highest peak in the wave number range of 1,000 $cm^{-1}$ to 1,008 $cm^{-1}$ by the intensity of the highest peak in the wave number range of 1,023 $cm^{-1}$ to 1,031 $cm^{-1}$ is not greater than 0.5, then the item to be identified can be identified as a polystyrene that contains an ethylenebis series flame retardant.

After the step (ii), the plastic identifying method further may include:

(x) a step of obtaining a third infrared absorption spectrum by excluding from the peaks of the first infrared absorption spectrum the peaks of the infrared absorption spectrum of any plastic identified as contained in the item to be identified, and (y) a step of identifying a substance that is adhering to a surface of the item to be identified by matching the third infrared absorption spectrum with the group of infrared absorption spectra.

The above-mentioned adhering substances may be substances that contain at least one material selected from the group consisting of fats/oils, proteins, coatings, celluloses, and inorganic silicates.

In the step (y) of the plastic identifying method, when the third infrared absorption spectrum has a peak in the wave number range of 1,736 $cm^{-1}$ to 1,744 $cm^{-1}$, then the adhering substance can be identified as at least one material selected from the group consisting of fats/oils and coatings.

In the step (y) of the plastic identifying method, when the third infrared absorption spectrum has a peak in the wave number range of 1,646 $cm^{-1}$ to 1,654 $cm^{-1}$ and the wave number range of 1,541 $cm^{-1}$ to 1,549 $cm^{-1}$, then the adhering substance can be identified as a protein.

In the step (y) of the plastic identifying method, when the third infrared absorption spectrum has a peak in the wave number range of 1,000 $cm^{-1}$ to 1,100 $cm^{-1}$, then the adhering substance can be identified as at least one material selected from the group consisting of celluloses and inorganic silicates.

After the step (i), the plastic identifying method further may include:

(X) a step of obtaining a fourth infrared absorption spectrum by excluding the peaks of the first infrared absorption spectrum from the peaks of the second infrared absorption spectrum, and (Y) a step of identifying a substance that is adhering to a surface of the item to be identified by matching the fourth infrared absorption spectrum with the group of infrared absorption spectra.

After the step (i), the plastic identifying method may further include:

(s) a step of determining an area $D_1$ of the peaks in the first infrared absorption spectrum in the wave number range of 400 $cm^{-1}$ to 7,000 $cm^{-1}$, (t) a step of determining an area $D_2$ of the peaks in the second infrared absorption spectrum in the wave number range of 400 $cm^{-1}$ to 7,000 $cm^{-1}$, and (u) a step of determining a value D by dividing the area $D_2$ by the area $D_1$ ($D=D_2/D_1$).

After the step (ii), the plastic identifying method further may include:

(S) a step of establishing a first baseline of the first infrared absorption spectrum by joining with a straight line a peak in the first infrared absorption spectrum in the vicinity of the wave number 2,750 cm$^{-1}$ with a peak in the vicinity of the wave number 3,140 cm$^{-1}$, (T) a step of establishing a second baseline of the first infrared absorption spectrum by joining with a straight line a peak in the first infrared absorption spectrum in the vicinity of the wave number 3,663 cm$^{-1}$ with a peak in the vicinity of the wave number 3,791 cm$^{-1}$, and (U) a step of taking the peak intensity in the first infrared absorption spectrum in the vicinity of the wave number 2,920 cm$^{-1}$ as $H_1$ and the peak intensity in the vicinity of the wave number 3,750 cm$^{-1}$ as $H_2$, and determining a value H by dividing the $H_2$ by the $H_1$. Note that the $H_1$ is the peak intensity of the first infrared absorption spectrum relative to the first baseline, and that the $H_2$ is the peak intensity of the first infrared absorption spectrum relative to the second baseline.

BEST MODE FOR CARRYING OUT THE INVENTION

Referring to the accompanying drawings, the following is an explanation of embodiments of the present invention. It should be noted that in the following embodiments, the same components are referred to by the same reference numerals, and duplicate explanations are sometimes omitted.

Embodiment 1

The plastic identifying method of the present invention includes:

(i) a step of obtaining a first infrared absorption spectrum by irradiating infrared light of a predetermined wave number onto an item to be identified that contains plastic and measuring the intensity of the infrared light that is totally reflected by this item, and;

(ii) a step of identifying the plastic contained in the item to be identified by matching the first infrared absorption spectrum with a group of infrared absorption spectra that have been measured for a group of predetermined materials.

The group of predetermined materials mentioned above is a group of materials containing plastics. Each infrared absorption spectrum in this group of infrared absorption spectra is obtained by irradiating infrared light of a predetermined wave number onto each material included in the group of predetermined materials, and measuring the intensity of the infrared light that is totally reflected by that material. Matching is then carried out by comparing peaks in the first infrared absorption spectrum with peaks in each infrared absorption spectrum in the group of infrared absorption spectra.

With the plastic identifying method, the plastic contained in an item to be identified can be identified with very good accuracy, even when the item to be identified has been colored, or even when the item to be identified contains a flame retardant.

Figure 1:
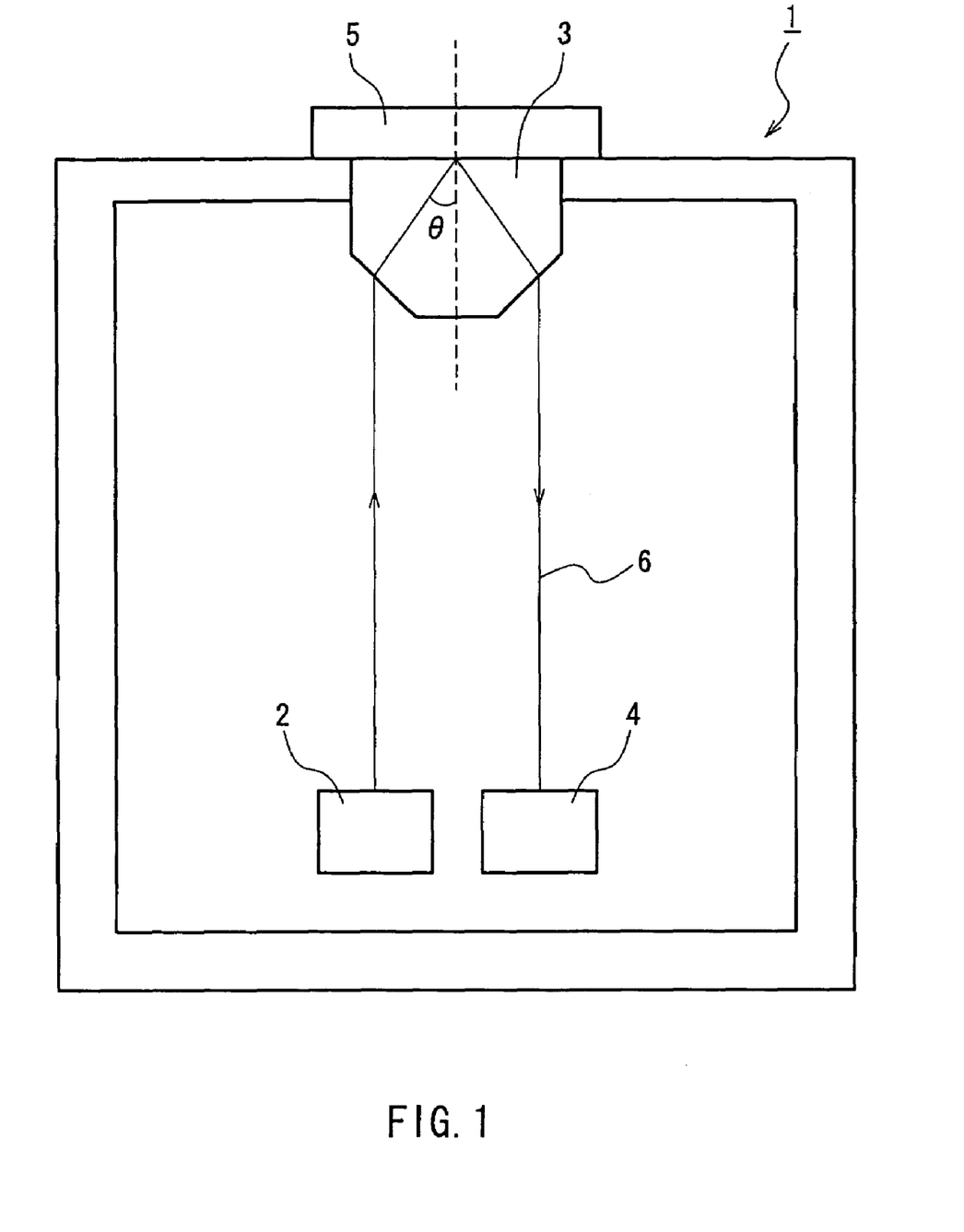
FIG. 1 is a cross-sectional view showing an example of a detection unit that can implement the plastic identifying method of the present invention.

There is no particular limitation to the method of carrying out the step (i) in the plastic identifying method. For example, a detection unit combining items such as an infrared light source, lenses, a prism, and a detection device may be used. An example of such a detection unit is shown in FIG. 1. It should be noted that the above-mentioned infrared light of a predetermined wave number (also referred to below as simply "infrared light") has a wave number in the range, for example, of 400 cm$^{-1}$ to 7,000 cm$^{-1}$ (which puts this light mainly into the category of mid-infrared light).

Shown in FIG. 1, a detection unit 1 is provided with a light source 2, a prism 3, and a detection device 4. Infrared light 6 emitted from the light source 2 is irradiated onto the item 5 to be identified by the prism 3. At this time, the incident light angle θ, which is shown in FIG. 1, should be set so as the infrared light 6 to be totally reflected by the surface of the item 5 to be identified. (The incident light angle θ should be greater than the critical angle of total reflectance for the infrared light 6). For example, the incident light angle θ may be set in the range of 30° to 85°. The intensity of the infrared light 6 that is totally reflected by the surface of the item 5 to be identified is measured by the detection device 4 after passing through the prism 3. It should be noted that FIG. 1 is a cross-sectional view in which hatching has been omitted in order to make the drawing easier to view.

Additionally, an ATR (attenuated total reflectance) method may be used as the method for causing total reflectance of infrared light from the surface of the item to be identified. In this measurement method, the infrared light absorption spectrum ("infrared light absorption spectrum" is also referred to hereinafter as simply "spectrum") can be obtained by using an ATR prism, which is a medium with a high refractive index, irradiating infrared light onto the surface of the item to be identified at an angle greater than the critical angle, and measuring the intensity of the totally reflected infrared light.

By using methods of totally reflecting infrared light from the surface of the item to be identified, the type of plastic contained in the item to be identified can be accurately identified even when the item to be identified has been colored.

There is no particular limitation to the method of carrying out the step (ii) in this identifying method. For example, it may involve first setting up a database or the like that records in advance the measured spectra of a predetermined group of materials, then matching them successively with the first spectrum obtained in the step (i). The predetermined group of materials should be a group of materials that contains plastic. Additionally, it is possible to use the same method as that described above in the step (i) for measuring the spectra of predetermined groups of materials.

Matching should be performed by comparing the peaks of the spectra that are to be contrasted. It is possible to compare the peaks, for example, in terms of peak position or peak intensity. This method may involve, for example, verifying whether or not a specific spectral peak of one of the above-mentioned spectra is present in the first spectrum, or by verifying the spectrum (differential spectrum) obtained by taking the difference between the spectra that are to be contrasted (if no peak is apparent in the differential spectrum, the two spectra to be contrasted can be considered approximately equivalent). As items to be identified for recycling exhibit various conditions of degradation, it is preferable to have a method that verifies whether or not a specific spectral peak is present in the first spectrum. The result of this matching is that, of the group of predetermined materials, the material exhibiting the spectrum best approximating the first spectrum can be taken as the type of plastic of the item to be identified.

The step (i) in the identifying method of the present invention may include:

(i-a) a step of sampling a test piece from the item to be identified, and (i-b) a step of obtaining the first infrared absorption spectrum by irradiating infrared light of a predetermined wave number onto the test piece, and measuring the intensity of the infrared light that is totally reflected by the test piece.

In an identifying method such as this, infrared light is not irradiated directly onto the item to be identified, but rather infrared light is irradiated onto a test piece that has been sampled from the item. For this reason, even when the actual item to be identified is very large, the identification process is simple. Furthermore, as the size and shape of the test pieces can be optimized to suit the detection unit regardless of the shape of the actual items to be identified, plastic types contained in the items to be identified can be identified accurately and consistently. This identifying method is also suitable for continuous identifying processes.

Moreover, the step (i) in the identifying method of the present invention may include:

(i-A) a step of sampling a test piece from the item to be identified, (i-B) a step of obtaining a second infrared absorption spectrum by irradiating infrared light of a predetermined wave number onto a first face of the test piece that corresponds to a surface of the item to be identified, and measuring the intensity of the infrared light that is totally reflected by the first area, and (i-C) a step of obtaining a first infrared absorption spectrum by irradiating infrared light of a predetermined wave number onto a second face of the test piece that was first exposed when the test piece was sampled, and measuring the intensity of the infrared light that is totally reflected by the second face.

In an identifying method such as this, spectral measurements are performed for at least two faces of the test pieces. Furthermore, one of the measured faces is a surface that was first exposed at the time of sampling. For this reason, the type of plastic contained in the item to be identified can be identified accurately and consistently even when the surface of the item to be identified has degraded due to use over a long period and even when grime and similar substances are adhering to the surface of the item to be identified. Additionally, as will be explained below, using this identifying method makes it possible to quantify the extent of dirt on the surface of items to be identified.

Figure 2:
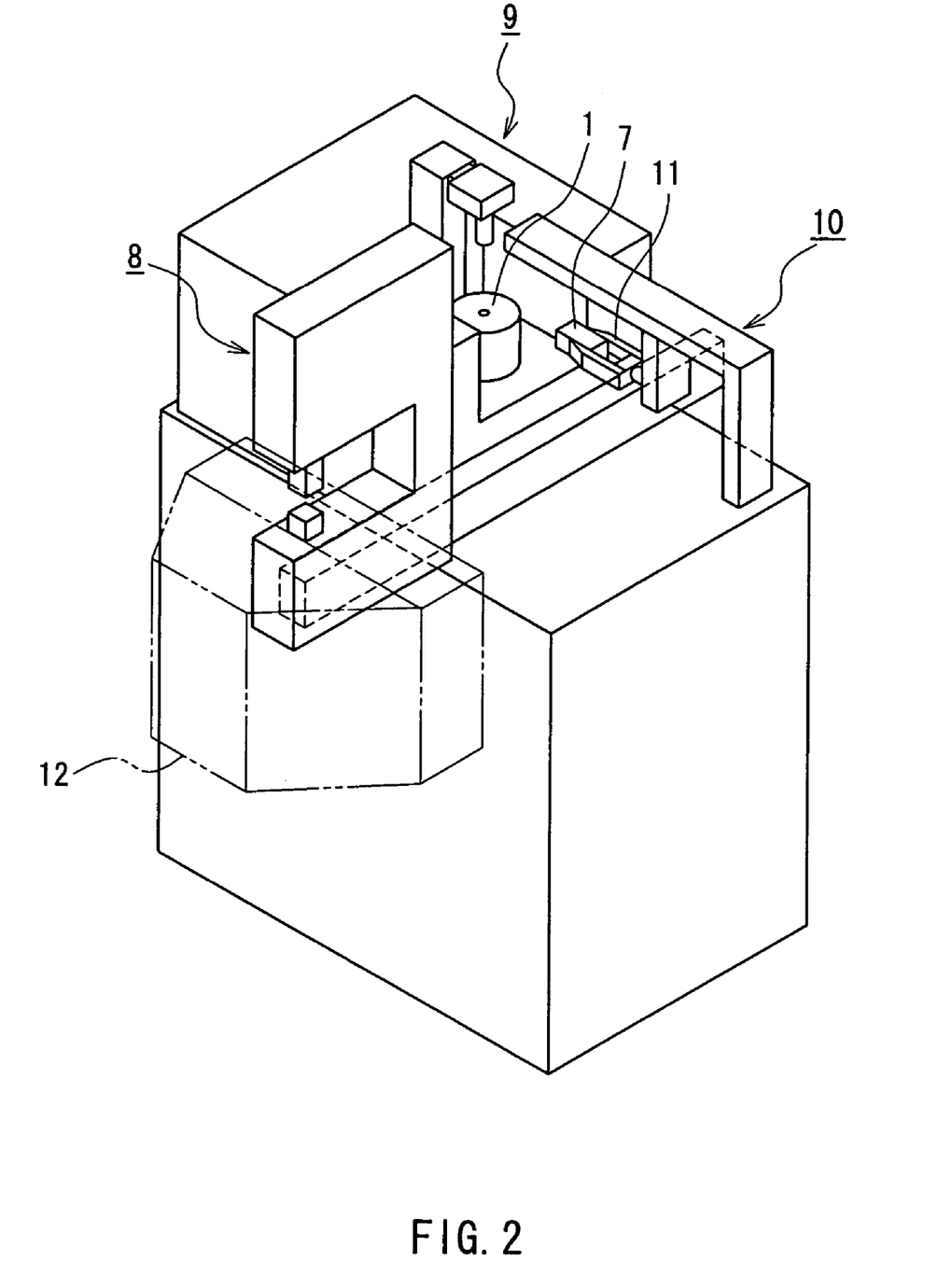
FIG. 2 is a schematic drawing showing an example of an identification apparatus that can implement the plastic identifying method of the present invention.

The identifying method can be implemented, for example, by using the identifying apparatus shown in FIG. 2. The identifying apparatus shown in FIG. 2 is provided with a sampling unit 8 that samples a test piece 7 from the item 12 to be identified, an identification unit 9 that is provided with a detection unit 1 for identifying the type of plastic contained in the test piece 7, and a transport unit 10 that transports the test piece from the sampling unit 8 to the detection unit 1.

The sampling unit 8 may be provided with, for example, a punch press. In this case, it is easy to sample the test piece 1. The identification unit 9 may be provided with, for example, the detection unit shown in FIG. 1. The transport unit 10 may be provided with, for example, a chucking unit 11. When the chucking unit 11 is provided, it is easier to measure the surfaces for two or more surfaces of the test piece 1. Additionally, the matching of the first spectrum with a group of spectra may be performed using the identification unit 9. In this case, the data for the group of spectra may be recorded in advance in the identification unit 9, then after the first spectrum is measured by the detection unit 4, the first spectrum data can be sent to the identification unit 9 and matched.

In the identifying method of the present invention, the predetermined group of materials may be the group of materials that contains at least one material selected from the group consisting of acrylonitrile-butadiene-styrene copolymer (ABS), polypropylene (PP), and polystyrene (PS). These plastics are very often used in the chassis of household electrical appliances and the like.

In the identifying method of the present invention, the predetermined group of materials may be a group of materials containing plastic that contains a flame retardant. In fact, the plastic contained in items to be identified for recycling very often contains flame retardants. When the plastic contained in an item to be identified contains flame retardants, it is sometimes difficult to identify the plastic type merely by matching the first measured spectrum with a group of spectra of standard plastics. For that purpose, with an identifying method such as this, even when the item to be identified contains flame retardants, the type of plastic contained in item to be identified can be identified accurately.

In the identifying method, plastics that contain flame retardants may be an ABS that contains a tetrabromobisphenol A (TBA) series flame retardant. Moreover, the plastics that contain flame retardants may be a PS that contains at least one type of the flame retardant selected from the group consisting of decabrominated flame retardants, TBA series flame retardants, triazine series flame retardants, and ethylenebis series flame retardants. These plastics are very often used in the chassis of household electrical appliances and the like.

In the step (ii) in the identifying method of the present invention, when the first infrared absorption spectrum has a peak in the wave number range of 906 cm$^{-1}$ to 914 cm$^{-1}$, the wave number range of 1,023 cm$^{-1}$ to 1,031 cm$^{-1}$, and the wave number range of 2,234 cm$^{-1}$ to 2,242 cm$^{-1}$, and the value obtained by dividing the highest peak intensity in the wave number range of 1,000 cm$^{-1}$ to 1,008 cm$^{-1}$ by the highest peak intensity in the wave number range of 1,023 cm$^{-1}$ to 1,031 cm$^{-1}$ is not greater than 0.5, then the item to be identified may be identified as an ABS. It should be noted that the reason for allowing some width in the peak wave numbers used for identification is due to consideration for the effects of such factors as measurement error and peak shifts caused by additives, and the like.

Table 1 below shows a compilation of the ABS identifying method. The R value in Table 1 is the value obtained by dividing the highest peak intensity in the wave number range of 1,000 cm$^{-1}$ to 1,008 cm$^{-1}$ by the highest peak intensity in the wave number range of 1,023 cm$^{-1}$ to 1,031 cm$^{-1}$. It should be noted that the R values in this specification all indicate this value.

TABLE 1

| Plastic type to be identified | Range of wave number (cm$^{-1}$) used for identification and peak yes/no | R value |
|---|---|---|
| ABS | 906 to 914: yes<br>1,023 to 1,031: yes<br>2,234 to 2,242: yes | R ≤ 0.5 |

In the step (ii) in the identifying method of the present invention, identification may be performed as shown in Table 2 below. The format of Table 2 is the same as Table 1 above. Specifically, for example, when the first infrared absorption spectrum in the step (ii) has a peak in the wave number range of 1,373 cm$^{-1}$ to 1,381 cm$^{-1}$, the wave number range of 2,913 cm$^{-1}$ to 2,921 cm$^{-1}$, and the wave number range of 2,946 cm$^{-1}$ to 2,954 cm$^{-1}$, then the item to be identified can be identified as a PP. It should be noted that the identifying method for ABS shown in Table 1 is also listed in Table 2.

TABLE 2

| Plastic type to be identified | Range of wave number (cm$^{-1}$) used for identification and peak yes/no | R value |
|---|---|---|
| ABS | 906 to 914: yes<br>1,023 to 1,031: yes<br>2,234 to 2,242: yes | R ≤ 0.5 |
| PP | 1,373 to 1,381: yes<br>2,913 to 2,921: yes<br>2,946 to 2,954: yes | Not used in identification |
| PS (not containing TBA series flame retardants) | 1,368 to 1,376: yes<br>1,023 to 1,031: yes | R ≤ 0.5 |
| PS (not containing flame retardants) | 1,368 to 1,376: yes<br>1,023 to 1,031: yes<br>1,348 to 1,356: no | R ≤ 0.5 |
| PS (containing decabrominated flame retardants) | 1,349 to 1,357: yes<br>1,023 to 1,031: yes<br>907 to 915: no | R ≤ 0.5 |
| PS (containing TBA series flame retardants) | 1,000 to 1,008: yes<br>1,023 to 1,031: yes | R ≥ 0.5 |
| PS (containing triazine series flame retardants) | 1,356 to 1,364: yes<br>1,227 to 1,235: yes<br>1,085 to 1,093: yes<br>1,023 to 1,031: yes | R ≤ 0.5 |
| PS (containing ethylenebis series flame retardants) | 1,369 to 1,377: yes<br>1,137 to 1,145: yes<br>742 to 750: yes<br>1,023 to 1,031: yes | R ≤ 0.5 |

The following is an explanation of the value R. As ABS and PS are plastics that contain styrene, they have a peak in the vicinity of the wave number 1,027 cm$^{-1}$. On the other hand, ABS and PS sometimes contain TBA series flame retardants as additives, and when they contain a TBA series flame retardant, a peak appears in the vicinity of the wave number 1,004 cm$^{-1}$. However, even when they do not contain a TBA series flame retardant, a peak sometimes appears in the vicinity of the wave number 1,004 cm$^{-1}$ due to such factors as the other substances contained in items to be identified and measurement error, and therefore it is not always possible to be certain whether a plastic contains TBA series flame retardants or not based on only whether there is a peak in the vicinity of the wave number 1,004 cm$^{-1}$. It is for this reason that, in the identifying method of the present invention, the value R is determined, which is the ratio of the highest peak intensity in the wave number range of 1,000 cm$^{-1}$ to 1,008 cm$^{-1}$ with the highest peak intensity in the wave number range of 1,023 cm$^{-1}$ to 1,031 cm$^{-1}$. This method makes it possible to identify whether ABS or PS materials contain TBA series flame retardants reliably.

The following is an explanation with a specific example of how the first spectrum measured for the item to be identified and the group of spectra are matched.

Figure 3:
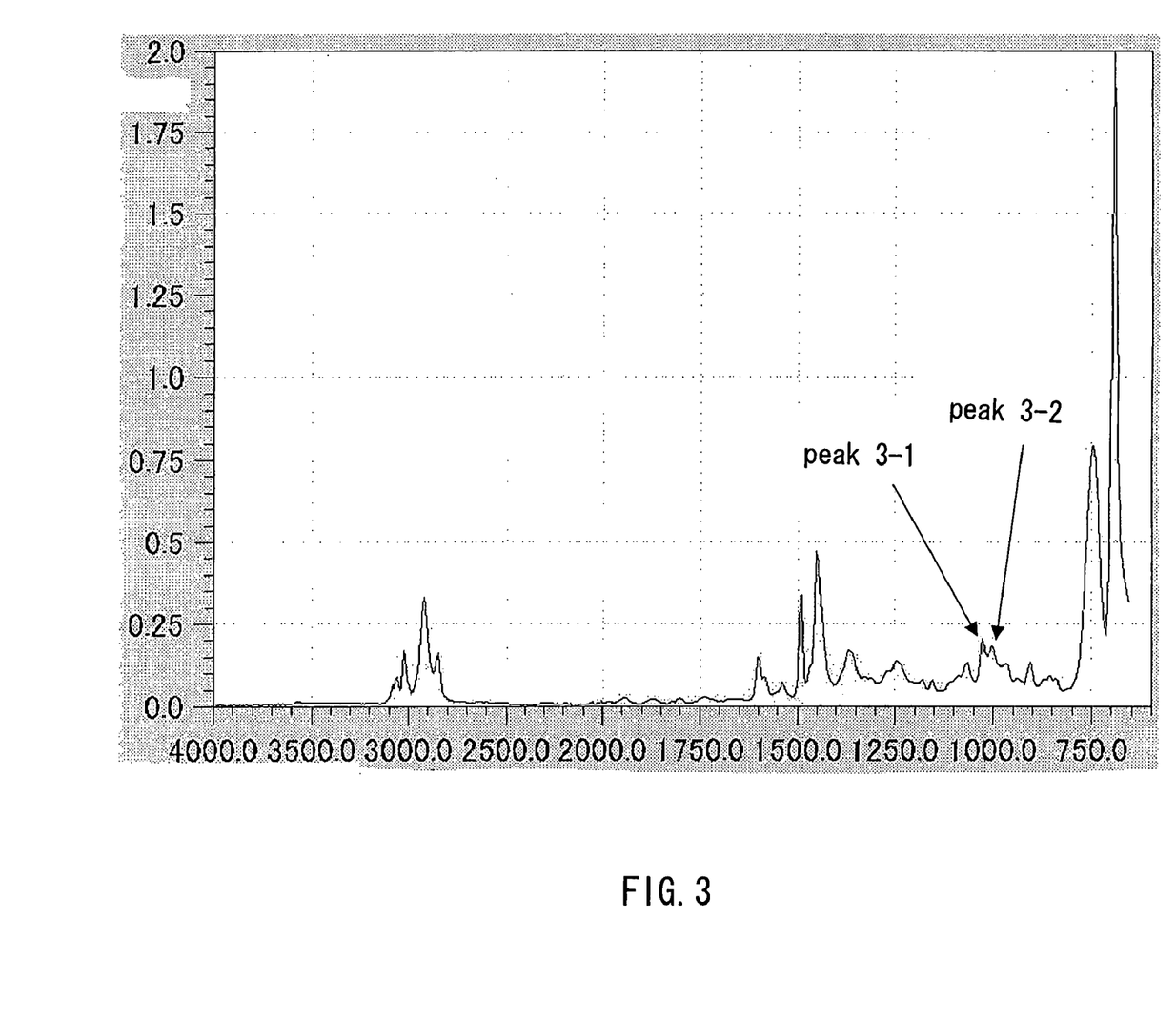
FIG. 3 shows an example of an infrared absorption spectrum measured using the plastic identifying method of the present invention.
Figure 4:
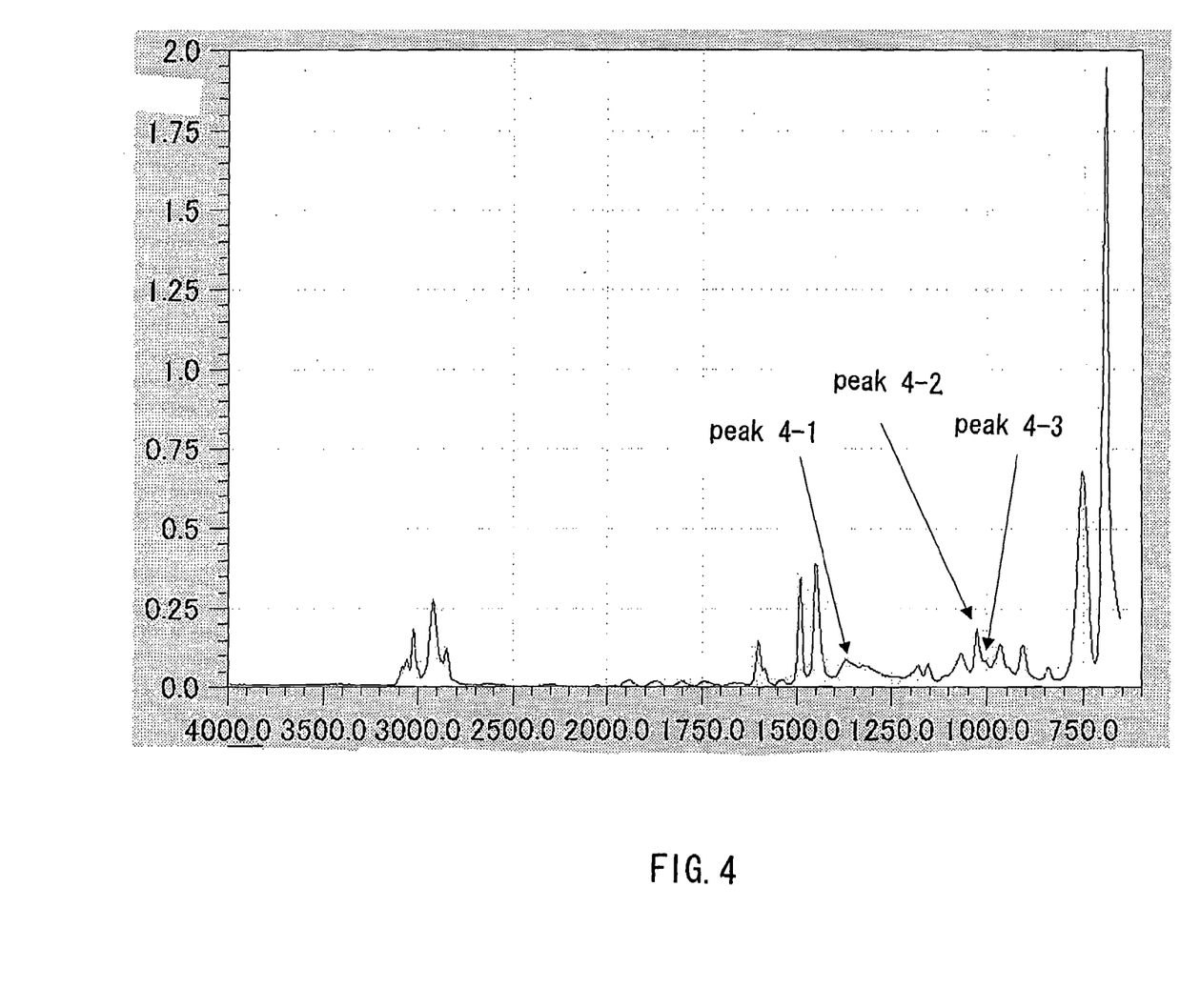
FIG. 4 shows another example of an infrared absorption spectrum measured using the plastic identifying method of the present invention.

The spectra shown in FIGS. 3 and 4 are each a first spectrum for different items to be identified obtained by carrying out the step (i).

The spectrum shown in FIG. 3 has peaks at the wave number 1,027 cm$^{-1}$ and the wave number 1,004 cm$^{-1}$ (shown as peak 3-1 and peak 3-2 in FIG. 3). Furthermore, the value obtained by dividing the intensity of the highest peak in the wave number range of 1,000 cm$^{-1}$ to 1,008 cm$^{-1}$ (that is, peak 3-2) by the intensity of the highest peak in the wave number range of 1,023 cm$^{-1}$ to 1,031 cm$^{-1}$ (that is, peak 3-1) is approximately 0.8. Therefore, the item to be identified, whose measured spectrum is shown in FIG. 3, can be identified as a PS containing a TBA series flame retardant. It should be noted that, in the spectrum shown in FIG. 3, the horizontal axis is the infrared light wave number (cm$^{-1}$) and the vertical axis is light absorbance.

Next, the spectrum shown in FIG. 4 has peaks at the wave number 1,372 cm$^{-1}$ and the wave number 1,027 cm$^{-1}$ (shown as peak 4-1 and peak 4-2 in FIG. 4). Furthermore, the value obtained by dividing the intensity of the highest peak in the wave number range of 1,000 cm$^{-1}$ to 1,008 cm$^{-1}$ (that is, peak 4-3 in FIG. 4) by the intensity of the highest peak in the wave number range of 1,023 cm$^{-1}$ to 1,031 cm$^{-1}$ (that is, peak 4-2) is approximately 0.3. Therefore, the item to be identified, whose measured spectrum is shown in FIG. 4, can be identified as a PS not containing a TBA series flame retardant. It should be noted that, in the spectrum shown in FIG. 4, the horizontal axis is the infrared light wave number (cm$^{-1}$) and the vertical axis is light absorbance.

Embodiment 2

The following is an explanation of an example of an embodiment of the plastic identifying method of the present invention in which an item that has a substance adhering to its surface is identified.

After the step (ii), the identifying method of the present invention may further include:

(x) a step of obtaining a third infrared absorption spectrum by excluding from the peaks of the first infrared absorption spectrum the peaks of the infrared absorption spectrum of any plastic identified as contained in the item to be identified, and (y) a step of identifying a substance that is adhering to a surface of the item to be identified by matching the third infrared absorption spectrum with the group of infrared absorption spectra.

It is often the case that an item to be identified for recycling has various substances adhering to its surface, but with an identifying method such as this, it is possible to identify the substances that are adhering to the surface of the item to be identified.

There is no particular limitation to the method of obtaining the third spectrum in the step (x). For example, the differential spectrum may be obtained by subtracting from the first spectrum the spectrum of any plastic identified as included in the items to be identified. Furthermore, the matching of the third spectrum with the group of infrared absorption spectra can be the same matching method as that described in the first embodiment.

Moreover, the step (i) in the identifying method of the present invention may include:

(i-A) a step of sampling a test piece from the item to be identified, (i-B) a step of obtaining a second infrared absorption spectrum by irradiating infrared light of a predetermined wave number onto a first face of the test piece that corresponds to the surface of the item to be identified, and measuring the intensity of the infrared light that is totally reflected by the first face, and (i-C) a step of obtaining the first infrared absorption spectrum by irradiating infrared light of a predetermined wave number onto a second face of the test piece that was first exposed when the piece was sampled, and measuring the intensity of the infrared light that is totally reflected by the second face, and after the step (i), it further may include:

(X) a step of obtaining a fourth infrared absorption spectrum by excluding the peaks of the first infrared absorption spectrum from the peaks of the second infrared absorption spectrum, and (Y) a step of identifying a substance that is adhering to a surface of the item to be identified by matching the fourth infrared absorption spectrum with the group of infrared absorption spectra.

When a substance adheres to the surface of an item to be identified, the second spectrum can be considered to contain the spectrum of the substance, because the substance remains on the first face of the test piece sampled from the item to be identified. On the other hand, it can be assumed that no substance will be present on the second face, which is first exposed during sampling. Therefore, with an identifying method such as this, it is possible to identify the substances that are present on the surface of the item to be identified.

There is no particular limitation to the method for obtaining the fourth spectrum in the step (X). For example, the differential spectrum may be obtained by subtracting the first spectrum from the second spectrum. Furthermore, the matching of the fourth spectrum with the group of infrared absorption spectra that occurs in the step (Y) may be the same matching method as that described in the first embodiment. Likewise, the step (i) also may be the same method as that described in the first embodiment.

In the identifying method of the present invention, the above-mentioned substance may be one material selected from the group consisting of fats/oils, proteins, coatings, celluloses, and inorganic silicates. Such materials often adhere to items to be identified for recycling. It should be noted that acrylic resin-based protective films, for example, or similar materials used to protect the surfaces of items to be identified can be considered as coatings. Additionally, examples of proteins include hand grime and the like, examples of celluloses include lint and the like, and examples of inorganic silicates include dust.

The step (y) (and the step (Y)) in the identifying method of the present invention may be performed as shown in Table 3 below. The format of Table 3 is the same as Table 1 and Table 2 above. Note though, that the value R is not used in identifying the adhering substances. For example, when the third (or fourth) infrared absorption spectrum in the step (y) (or the step (Y)) has a peak in the wave number range of 1,736 cm$^{-1}$ to 1,744 cm$^{-1}$, the adhering substance can be identified as being at least one material of the group consisting of fats/oils and coatings.

TABLE 3

| Type of adhering material to be identified | Range of wave number (cm$^{-1}$) used for identification and peak yes/no |
| --- | --- |
| At least one selected from fats/oils and coatings | 1,736 to 1,744: yes |
| Proteins | 1,646 to 1,654: yes |
| | 1,541 to 1,549: yes |
| At least one selected from celluloses and inorganic silicates | 1,000 to 1,100: yes |

Embodiment 3

The following is an explanation of an example of an embodiment of the plastic identifying method of the present invention in which the extent of dirt on the surface of an item to be identified is quantified.

The step (i) in the identifying method of the present invention may include:

(i-A) a step of sampling a test piece from an item to be identified, (i-B) a step of obtaining a second infrared absorption spectrum by irradiating infrared light of a predetermined wave number onto a first face of the test piece that corresponds to a surface of the item to be identified, and measuring the intensity of the infrared light that is totally reflected by the first face, and (i-C) a step of obtaining the first infrared absorption spectrum by irradiating infrared light of a predetermined wave number onto a second face of the test piece that was first exposed when the piece was sampled, and measuring the intensity of the infrared light that is totally reflected by the second face, and it may further include:

(s) a step of determining an area $D_1$ of the peaks in the first infrared absorption spectrum in the wave number range of 400 cm$^{-1}$ to 7,000 cm$^{-1}$, (t) a step of determining an area $D_2$ of the peaks in the second infrared absorption spectrum in the wave number range of 400 cm$^{-1}$ to 7,000 cm$^{-1}$, and (u) a step of determining a value D by dividing the area $D_2$ by the area $D_1$ ($D=D_2/D_1$).

An item to be identified that has been recovered from the marketplace sometimes has dirt adhering to its surface. In cases when dirt is adhering in this way, reliable spectra cannot be obtained simply by measuring the spectrum of the item to be identified, and sometimes it is difficult to identify the type of plastic contained in the item. Therefore, by sampling a test piece from the item to be identified and measuring the spectra of a first face that corresponds to its surface (which is considered to have dirt adhering) and a second face that was first exposed at the time of sampling (considered not to have dirt adhering), and by quantifying the difference of the peak areas of their respective spectra, or specifically, determining the ratio of their peak areas, it is possible to quantify the extent of dirt adhering to the surface of the item to be identified (a coefficient of surface soiling). If the extent of dirt adhering to the surface of an item to be identified can be quantified, it is possible to identify with greater accuracy the type of plastic it contains. With the obtained coefficient of surface soiling value D, it is possible to perform processes such as removing an item from those targeted for recycling (for example, when D is equal to or less than 0.5).

It should be noted that there are no particular limitations to the methods for performing the steps (s), (t), and (u). For example, mathematical processing may be performed for each obtained spectrum. Additionally, the step (i) may also be the same method as that described in the first embodiment.

Embodiment 4

The following is an explanation of an example of an embodiment of the present invention that involves a method for verifying whether a reliable spectrum has been obtained or not when a spectrum is obtained from an item to be identified.

After the step (ii), the identifying method of the present invention may further include:

(S) a step of establishing a first baseline of the first infrared absorption spectrum by joining with a straight line a peak in the first infrared absorption spectrum in the vicinity of the wave number 2,750 cm$^{-1}$ with a peak in the vicinity of the wave number 3,140 cm$^{-1}$, (T) a step of establishing a second baseline of the first infrared absorption spectrum by joining with a straight line a peak in the first infrared absorption spectrum in the vicinity of the wave number 3,663 cm$^{-1}$ with a peak in the vicinity of the wave number 3,791 cm$^{-1}$, and (U) a step of taking the peak intensity in the first infrared absorption spectrum in the vicinity of the wave number 2,920 cm$^{-1}$ as $H_1$ and the peak intensity in the vicinity of the wave number 3,750 cm$^{-1}$ as $H_2$, and determining a value H by dividing the $H_2$ by the $H_1$. Note that the $H_1$ is the peak intensity of the first infrared absorption spectrum relative to the first baseline, and that the $H_2$ is the peak intensity of the first infrared absorption spectrum relative to the second baseline.

A peak in the vicinity of the wave number 2,750 cm$^{-1}$ here means a peak around the wave number 2,750 cm$^{-1}$, including a range of ±4 cm$^{-1}$. Additionally, peak refers to the peak of the highest intensity in cases when there are multiple peaks within this range. The same judgement should also be performed for the peaks measured at other vicinities of wave number in the steps (S), (T), and (U).

When measuring the infrared absorption spectra of an item to be identified, very accurate identification of the type of plastic contained in the item can be achieved if reliable contact is made between the detection unit, which irradiates onto the item to be identified and measures the intensity of the infrared light that is totally reflected by the surface of the item to be identified, and the item to be identified. For this reason, there is a need for a method that verifies whether the detection unit and the item to be identified are reliably in contact.

When contact between the item to be identified and the detection unit is incomplete, there is a layer of air between them. Because water vapor is contained in this layer of air, the condition of the contact between the item to be identified and the detection unit can be verified by analyzing the extent to which the spectrum of water vapor is contained in the spectrum measured for the item to be identified.

Therefore, by dividing $H_2$, the intensity of the peak in the vicinity of the wave number 3,750 cm$^{-1}$, which corresponds to that of water vapor, by $H_1$, the intensity of the peak in the vicinity of the wave number 2,920 cm$^{-1}$, which is a reference for resin identification, and thereby obtaining the value H, it is possible to verify the condition of the contact between the item to be identified and the detection unit. For example, if the value H is at least 0.3, the peak intensity of the water vapor can be diagnosed as high, and the contact between the item to be identified and the detection unit can be diagnosed as incomplete. In this case, the position of the item to be identified can be adjusted and measurements retaken. Furthermore, if the value H is lower than 0.3, the process may proceed to identify the type of plastic contained in the item to be identified.

It should be noted that there is no particular limitation to the method for performing the steps (S), (T), and (U). For example, mathematical processing may be performed for each obtained spectrum.

The present invention may be embodied in other specific forms without departing from the spirit or essential characteristics thereof. The embodiments disclosed in this application are to be considered in all respects as illustrative and not restrictive, the scope of the invention being indicated by the appended claims rather than by the foregoing description. All changes that come within the meaning and range of equivalency of the claims are intended to be embraced therein.

INDUSTRIAL APPLICABILITY

As shown above, with the plastic identifying method of the present invention, the type of plastic contained in an item can be identified accurately even when the item to be identified has been colored or contains additives or the like.

The invention claimed is:

1. A plastic material identifying method comprising:
(i) a step of obtaining a first infrared absorption spectrum by irradiating infrared light of a predetermined wave number onto an item to be identified that contains a plastic material and measuring the intensity of the infrared light that is totally reflected by the item; and
(ii) a step of identifying the plastic material contained in the item to be identified by matching the first infrared absorption spectrum with a group of infrared absorption spectra that have been measured for a predetermined group of materials;
wherein the predetermined group of materials is a group of materials containing plastics; and
each infrared absorption spectrum in the group of infrared absorption spectra is obtained by irradiating infrared light of a predetermined wave number onto each material included in the group of predetermined materials, and measuring the intensity of the infrared light that is totally reflected by the material; and
matching is carried out by comparison between the first infrared absorption spectrum and each infrared absorption spectrum in the group of infrared absorption spectra in terms of presence or absence of a peak in a predetermined wave number range and by comparison between the first infrared absorption spectrum and each infrared absorption spectrum in the group of infrared absorption spectra in terms of a value obtained by dividing a highest peak intensity in a wave number range of 1,000 cm$^{-1}$ to 1,008 cm$^{-1}$ by a highest peak intensity in a wave number range of 1,023 cm$^{-1}$ to 1,031 cm$^{-1}$.

2. The plastic material identifying method according to claim 1,
wherein the step (i) comprises:
(i-a) a step of sampling a test piece from the item to be identified; and
(i-b) a step of obtaining the first infrared absorption spectrum by irradiating infrared light of a predetermined wave number onto the test piece, and measuring the intensity of the infrared light that is totally reflected by the test piece.

3. The plastic material identifying method according to claim 1,
wherein the step (i) comprises:
(i-A) a step of sampling a test piece from the item to be identified;
(i-B) a step of obtaining a second infrared absorption spectrum by irradiating infrared light of a predetermined wave number onto a first face of the test piece that corresponds to a surface of the item to be identified, and measuring the intensity of the infrared light that is totally reflected by the first face; and
(i-C) a step of obtaining the first infrared absorption spectrum by irradiating infrared light of a predetermined wave number onto a second face of the test piece that was first exposed when the test piece was sampled, and measuring the intensity of the infrared light that is totally reflected by the second face.

4. The plastic material identifying method according to claim 1,
wherein the predetermined group of materials is a group of materials that contains at least one material selected from the group consisting of acrylonitrile-butadiene-styrene copolymers, polypropylenes, and polystyrenes.

5. The plastic material identifying method according to claim 1,
wherein the predetermined group of materials is a group of materials containing plastics that contain flame retardants.

6. The plastic material identifying method according to claim 5,
wherein the plastics that contain flame retardants are acrylonitrile-butadiene-styrene copolymers that contain tetrabromobisphenol A series flame retardants.

7. The plastic material identifying method according to claim 5,
wherein the plastics that contain flame retardants are polystyrenes that contain at least one of the flame retardants selected from the group consisting of decabrominated flame retardants, tetrabromobisphenol A series flame retardants, triazine series flame retardants, and ethylenebis series flame retardants.

8. The plastic material identifying method according to claim 1,
wherein the item to be identified is identified as an acrylonitrile-butadiene-styrene copolymer in the step (ii) when:
the first infrared absorption spectrum has a peak in the wave number range of 906 $cm^{-1}$ to 914 $cm^{-1}$, the wave number range of 1,023 $cm^{-1}$ to 1,031 $cm^{-1}$, and the wave number range of 2,234 $cm^{-1}$ to 2,242 $cm^{-1}$; and
the value obtained by dividing the highest peak intensity in the wave number range of 1,000 $cm^{-1}$ to 1,008 $cm^{-1}$ by the highest peak intensity in the wave number range of 1,023 $cm^{-1}$ to 1,031 $cm^{-1}$ is not greater than 0.5.

9. The plastic material identifying method according to claim 1,
wherein the item to be identified is identified as a polypropylene in the step (ii) when:
the first infrared absorption spectrum has a peak in the wave number range of 1,373 $cm^{-1}$ to 1,381 $cm^{-1}$, the wave number range of 2,913 $cm^{-1}$ to 2,921 $cm^{-1}$, and the wave number range of 2,946 $cm^{-1}$ to 2,954 $cm^{-1}$.

10. The plastic material identifying method according to claim 1,
wherein the item to be identified is identified as a polystyrene that does not contain a tetrabromobisphenol A series flame retardant in the step (ii) when:
the first infrared absorption spectrum has a peak in the wave number range of 1,368 $cm^{-1}$ to 1,376 $cm^{-1}$ and the wave number range of 1,023 $cm^{-1}$ to 1,031 $cm^{-1}$;
and the value obtained by dividing the intensity of the highest peak in the wave number range of 1,000 $cm^{-1}$ to 1,008 $cm^{-1}$ by the intensity of the highest peak in the wave number range of 1,023 $cm^{-1}$ to 1,031 $cm^{-1}$ is not greater than 0.5.

11. The plastic material identifying method according to claim 1,
wherein the item to be identified is identified as a polystyrene that does not contain a flame retardant in the step (ii) when:
the first infrared absorption spectrum has a peak in the wave number range of 1,368 $cm^{-1}$ to 1,376 $cm^{-1}$ and the wave number range of 1,023 $cm^{-1}$ to 1,031 $cm^{-1}$;
and
does not have a peak in the wave number range of 1,348 $cm^{-1}$ to 1,356 $cm^{-1}$;
and
the value obtained by dividing the intensity of the highest peak in the wave number range of 1,000 $cm^{-1}$ to 1,008 $cm^{-1}$ by the intensity of the highest peak in the wave number range of 1,023 $cm^{-1}$ to 1,031 $cm^{-1}$ is not greater than 0.5.

12. The plastic material identifying method according to claim 1,
wherein the item to be identified is identified as a polystyrene that contains decabrominated flame retardant in the step (ii) when:
the first infrared absorption spectrum has a peak in the wave number range of 1,349 $cm^{-1}$ to 1,357 $cm^{-1}$ and the wave number range of 1,023 $cm^{-1}$ to 1,031 $cm^{-1}$
and
does not have a peak in the wave number range of 907 $cm^{-1}$ to 915 $cm^{-1}$;
and
the value obtained by dividing the intensity of the highest peak in the wave number range of 1,000 $cm^{-1}$ to 1,008 $cm^{-1}$ by the intensity of the highest peak in the wave number range of 1,023 $cm^{-1}$ to 1,031 $cm^{-1}$ is not greater than 0.5.

13. The plastic material identifying method according to claim 1,
wherein the item to be identified is identified as a polystyrene that contains a tetrabromobisphenol A series flame retardant in the step (ii) when:
the first infrared absorption spectrum has a peak in the wave number range of 1,000 $cm^{-1}$ to 1,008 $cm^{-1}$ and the wave number range of 1,023 $cm^{-1}$ to 1,031 $cm^{-1}$;
and
the value obtained by dividing the intensity of the highest peak in the wave number range of 1,000 $cm^{-1}$ to 1,008 $cm^{-1}$ by the intensity of the highest peak in the wave number range of 1,023 $cm^{-1}$ to 1,031 $cm^{-1}$ is at least 0.5.

14. The plastic material identifying method according to claim 1,
wherein the item to be identified is identified as a polystyrene that contains a triazine series flame retardant in the step (ii) when:

the first infrared absorption spectrum has a peak in the wave number range of 1,356 cm$^{to}$ 1,364 cm$^{-1}$, the wave number range of 1,227 cm$^{-1}$ to 1,235 cm$^{-}$, the wave number range of 1,085 cm$^{-1}$ to 1,093 cm$^{-1}$, and the wave number range of 1,023 cm$^{-1}$ to 1,031 cm$^{-1}$; and the value obtained by dividing the intensity of the highest peak in the wave number range of 1,000 cm$^{-1}$ to 1,008 cm$^{-1}$ by the intensity of the highest peak in the wave number range of 1,023 cm$^{-1}$ to 1,031 cm$^{-1}$ is not greater than 0.5.

15. The plastic material identifying method according to claim 1, wherein the item to be identified is identified as a polystyrene that contains an ethylenebis series flame retardant in the step (ii) when:

the first spectrum has a peak in the wave number range of 1,369 cm$^{-1}$ to 1,377 cm$^{-1}$, the wave number range of 1,137 cm$^{-1}$ to 1,145 cm$^{-1}$, the wave number range of 742 cm$^{-1}$ to 750 cm$^{-1}$, and the wave number range of 1,023 cm$^{-1}$ to 1,031 cm$^{-1}$; and the value obtained by dividing the intensity of the highest peak in the wave number range of 1,000 cm$^{-1}$ to 1,008 cm$^{-1}$ by the intensity of the highest peak in the wave number range of 1,023 cm$^{-1}$ to 1,031 cm$^{-1}$ is not greater than 0.5.

16. The plastic material identifying method according to claim 1, that, after the step (ii), further comprises:

(x) a step of obtaining a third infrared absorption spectrum by excluding from the peaks of the first infrared absorption spectrum the peaks of the infrared absorption spectrum of any plastic material identified as contained in the item to be identified; and (y) a step of identifying a substance that is adhering to a surface of the item to be identified by matching the third infrared absorption spectrum with the group of infrared absorption spectra.

17. The plastic material identifying method according to claim 16, wherein the adhering substance is at least one material selected from the group consisting of fats/oils, proteins, coatings, celluloses, and inorganic silicates.

18. The plastic material identifying method according to claim 16, wherein, in the step (y), the adhering substance is identified as at least one material selected from the group consisting of fats/oils and coatings when:

the third infrared absorption spectrum has a peak in the wave number range of 1,736 cm$^{-1}$ to 1,744 cm$^{-1}$.

19. The plastic material identifying method according to claim 16, wherein, in the step (y), the adhering substance is identified as a protein when:

the third infrared absorption spectrum has a peak in the wave number range of 1,646 cm$^{-1}$ to 1,654 cm$^{-1}$ and the wave number range of 1,541 cm$^{-1}$ to 1,549 cm$^{-1}$.

20. The plastic material identifying method according to claim 16, wherein, in the step (y), the adhering substance is identified as at least one of the group consisting of celluloses and inorganic silicates when:

the third infrared absorption spectrum has a peak in the wave number range of 1,000 cm$^{-1}$ to 1,100 cm$^{-1}$.

21. The plastic material identifying method according to claim 3, that, after the step (i), further comprises:

(X) a step of obtaining a fourth infrared absorption spectrum by excluding the peaks of the first infrared absorption spectrum from the peaks of the second infrared absorption spectrum, and (Y) a step of identifying a substance that is adhering to a surface of the item to be identified by matching the fourth infrared absorption spectrum with the group of infrared absorption spectra.

22. The plastic material identifying method according to claim 3, that, after the step (i), further comprises:

(s) a step of determining an area $D_1$ of the peaks in the first infrared absorption spectrum in the wave number range of 400 cm$^{-1}$ to 7,000 cm$^{-1}$;

(t) a step of determining an area $D_2$ of the peaks in the second infrared absorption spectrum in the wave number range of 400 cm$^{-1}$ to 7,000 cm$^{-1}$; and (u) a step of determining a value D by dividing the area $D_2$ by the area $D_1$.

23. The plastic material identifying method according to claim 1, that, after the step (ii), further comprises:

(S) a step of establishing a first baseline of the first infrared absorption spectrum by joining with a straight line a peak in the first infrared absorption spectrum in a wave number range of 2,750±4 cm$^{-1}$ with a peak in a wave number range of 3,140±4 cm$^{-1}$;

(T) a step of establishing a second baseline of the first infrared absorption spectrum by joining with a straight line a peak in the first infrared absorption spectrum in a wave number range of 3,663±4 cm$^{-1}$ with a peak in a wave number range of 3,791±4 cm$^{-1}$; and (U) a step of taking the peak intensity in the first infrared absorption spectrum in a wave number range of 2,920±4 cm$^{-1}$ as $H_1$ and the peak intensity in a wave number range of 3,750±4 cm$^{-1}$ as $H_2$, and determining a value H by dividing the $H_2$ by the $H_1$;

wherein the $H_1$ is the peak intensity of the first infrared absorption spectrum relative to the first baseline, and the $H_2$ is the peak intensity of the first infrared absorption spectrum relative to the second baseline.

* * * * *

UNITED STATES PATENT AND TRADEMARK OFFICE
CERTIFICATE OF CORRECTION

PATENT NO. : 7,161,151 B2 Page 1 of 1
APPLICATION NO. : 10/476637
DATED : January 9, 2007
INVENTOR(S) : Irie et al.

It is certified that error appears in the above-identified patent and that said Letters Patent is hereby corrected as shown below:

Column 4, line 1: "1,000cm$^{-1}$" should read --1,000 cm$^{-1}$--.
Column 8, line 35: "contained in item" should read --contained in the item--.
Column 15, line 52(claim 1): "909 cm$^{-1}$ $^{to}$ 914 cm$^{-1}$" should read --909 cm$^{-1}$ to 914 cm$^{-1}$--.
Column 16, line 8(claim 10): "1,031 cm$^{-}$" should read --1,031 cm$^{-1}$ --.
Column 16, line 9(claim 10): a line break should occur between "and" and "the" so that --the value obtained-- begins on a new line.
Column 16, line 38(claim 12): "1,031 cm$^{-1}$ " should read --1,031 cm$^{-1}$--.
Column 17, line 2(claim 14): "1,356 cm$^{to}$ 1,364 cm$^{-1}$" should read --1,356 cm$^{-1}$ to 1,364 cm$^{-1}$ --.
Column 17, line 3(claim 14): "1,235 cm$^{-}$" should read --1,235 cm$^{-1}$ --.

Signed and Sealed this

Sixteenth Day of October, 2007

JON W. DUDAS
*Director of the United States Patent and Trademark Office*

UNITED STATES PATENT AND TRADEMARK OFFICE
CERTIFICATE OF CORRECTION

PATENT NO.         : 7,161,151 B2                                    Page 1 of 1
APPLICATION NO. : 10/476637
DATED              : January 9, 2007
INVENTOR(S)        : Irie et al.

It is certified that error appears in the above-identified patent and that said Letters Patent is hereby corrected as shown below:

Column 4, line 1: "1,000cm$^{-1}$" should read --1,000 cm$^{-1}$--.
Column 8, line 35: "contained in item" should read --contained in the item--.
Column 15, line 52(claim 8): "906 cm$^{-1}$ $^{to}$ 914 cm$^{-1}$" should read --906 cm$^{-1}$ to 914 cm$^{-1}$--.
Column 16, line 8(claim 10): "1,031 cm$^{-}$" should read --1,031 cm$^{-1}$--.
Column 16, line 9(claim 10): a line break should occur between "and" and "the" so that --the value obtained-- begins on a new line.
Column 16, line 38(claim 12): "1,031 cm$^{-1}$" should read --1,031 cm$^{-1}$;--.
Column 17, line 2(claim 14): "1,356 cm$^{to}$ 1,364 cm$^{-1}$" should read --1,356 cm$^{-1}$ to 1,364 cm$^{-1}$--.
Column 17, line 3(claim 14): "1,235 cm$^{-}$" should read --1,235 cm$^{-1}$--.

Signed and Sealed this

Twenty-third Day of October, 2007

JON W. DUDAS
*Director of the United States Patent and Trademark Office*